(12) United States Patent
Shacham-Diamand et al.

(10) Patent No.: US 9,517,020 B2
(45) Date of Patent: Dec. 13, 2016

(54) IL-1 RECEPTOR ANTAGONIST-COATED ELECTRODE AND USES THEREOF

(75) Inventors: Yosi Shacham-Diamand, Zichron-Ya'acov (IL); Matti Mintz, Tel Aviv (IL); Aryeh Taub, Rehovot (IL)

(73) Assignee: RAMOT AT TEL AVIV UNIVERSITY LTD., Tel Aviv (IL)

( * ) Notice: Subject to any disclaimer, the term of this patent is extended or adjusted under 35 U.S.C. 154(b) by 295 days.

(21) Appl. No.: 14/236,853

(22) PCT Filed: Jul. 23, 2012

(86) PCT No.: PCT/IL2012/050266
§ 371 (c)(1),
(2), (4) Date: May 21, 2014

(87) PCT Pub. No.: WO2013/018088
PCT Pub. Date: Feb. 7, 2013

(65) Prior Publication Data
US 2014/0249396 A1    Sep. 4, 2014

Related U.S. Application Data

(60) Provisional application No. 61/515,111, filed on Aug. 4, 2011.

(51) Int. Cl.
*A61B 5/0478* (2006.01)
*A61N 1/05* (2006.01)
(Continued)

(52) U.S. Cl.
CPC ......... *A61B 5/04001* (2013.01); *A61B 5/0478* (2013.01); *A61B 5/4836* (2013.01);
(Continued)

(58) Field of Classification Search
CPC .................................................. A61B 5/04001
See application file for complete search history.

(56) References Cited

U.S. PATENT DOCUMENTS 8,355,768 B2 * 1/2013 Masmanidis ...... A61B 5/04001
600/372
8,954,142 B2 * 2/2015 Ek ...................... A61B 5/04001
604/164.01
(Continued)

OTHER PUBLICATIONS

Zhong et al, "Dexamethasone-coated neural . . .porbes", Brain Research, 2007, 1148, 15-27.*
(Continued)

*Primary Examiner* — Lee S Cohen
(74) *Attorney, Agent, or Firm* — Knobbe Martens Olson & Bear LLP (57) ABSTRACT

The present invention provides an electrode designed for implantation into the central nervous system (CNS) of a mammal, wherein said electrode is substantially coated with interleukin-1 receptor antagonist (IL-1ra) or a coating composition comprising it, and the IL-1ra actively inhibits scarring on or around the surface of the electrode when implanted into the CNS. The electrode of the invention may be used for brain recording and/or stimulation, and can thus be used for treatment of a brain dysfunction, a brain disease or disorder, or a brain injury, as well as for brain computer interface, brain machine interface, or electrotherapy.

22 Claims, 5 Drawing Sheets

(51) Int. Cl.
- *A61B 5/04* (2006.01)
- *A61L 31/16* (2006.01)
- *A61B 5/00* (2006.01)
- *A61L 27/28* (2006.01)

(52) U.S. Cl.
CPC ............ *A61B 5/6868* (2013.01); *A61L 27/28* (2013.01); *A61L 31/16* (2013.01); *A61N 1/0534* (2013.01)

(56) References Cited

U.S. PATENT DOCUMENTS

| | | |
|---|---|---|
| 2005/0149157 A1 | 7/2005 | Hunter et al. |
| 2005/0187600 A1* | 8/2005 | Hunter ................... A61K 38/17 607/115 |
| 2009/0280153 A1 | 11/2009 | Hunter et al. |

OTHER PUBLICATIONS

Taub et al., "Bioactive anti-inflammatory coating for chronic neural electrodes" Journal of Biomedical Materials Research Part A, pp. 1854-1858. (2012).
He et al., "A novel anti-inflammatory surface for neural electrodes" Advanced Materials 19, pp. 3529-3533. (2007).
Greenhalgh et al., "Rapid brain penetration of interleukin-1 receptor antagonist in rat cerebral ischaemia: pharmacokinetics, distribution, protection" British Journal of Pharmacology 160, pp. 153-159. (2010).
Sanderson et al., "Interleukin-1 receptor antagonist attenuates regional neuronal cell death and cognitive dysfunction after experimental brain injury" Journal of Cerebral Blood Flow and Metabolism 19, pp. 1118-1125. (1999).
Deleidi et al., "The toll-like receptor-3 agonist polyinosinic:polycytidylic acid triggers nigrostriatal dopaminergic degeneration" The Journal of Neuroscience, 30(48), pp. 16091-16101. (2010).
Lucas et al., "The role of inflammation in CNS injury and disease" British journal of Pharmacology 147,pp. S232-S240. (2006).
Gelderd et al., "The Effects of Interleukin-1 Receptor Antagonist Protein (IRAP) Infusion Following Spinal Chord Transection in Rats" Molecular and Chemical Neuropathology, 27(2), pp. 167-183. (1996).
Kim et al., "The effect of covalently immobilized rhIL-1ra-ELP fusion protein on the inflammatory profile of LPS-stimulated human monocytes" Biomaterials, 28(23), pp. 3369-3377. (2007).
Bendele et al., "Combination benefit of treatment with the cytokine inhibitors interleukin-1 receptor antagonist and PEGylated soluble tumor necrosis factor receptor type I in animal models of rheumatoid arthritis" Arthritis & Rheumatism 43(12), pp. 2648-2659. (2000).
Born, T.L et al., "Identification and characterization of two members of a novel class of the interleukin-1 receptor (IL-1R) family" Journal of Biological Chemistry, 275(39), pp. 29946-29954. (2000).
Eng et al., "GFAP and astrogliosis" Brain Pathology 4(3), pp. 229-237. (1994).
Giulian et al., "Phagocytic microglia release cytokines and cytotoxins that regulate the survival of astrocytes and neurons in culture" Neurochemistry International, 25(3), pp. 227-233 .(1994).
Griffith et al., "Long-term gliosis around chronically implanted platinum electrodes in the Rhesus macaque motor cortex" Neuroscience Letters, 406(1-2), pp. 81-86. (2006).
He et al., "Nanoscale laminin coating modulates cortical scarring response around implanted silicon microelectrode arrays" Journal of Neural Engineering, 3(4), pp. 316-326. (2006).
Kim et al., "Sustained release of dexamethasone from hydrophilic matrices using PLGA nanoparticles for neural drug delivery" Biomaterials, 27(15), pp. 3031-3037. (2006).
Morgan et al., "Basic calcium phosphate crystal-induced prostaglandin E2 production in human fibroblasts: role of cyclooxygenase 1, cyclooxygenase 2, and interleukin-1β" Arthritis & Rheum. 50(5), pp. 1642-1649. (2004).
Nordhausen et al., "Single unit recording capabilities of a 100 microelectrode array" Brain Research, 726(1-2), pp. 129-140. (1996).
Polikov et al., "Response of brain tissue to chronically implanted neural electrodes" Journal of Neuroscience Methods,148(1), pp. 1-18. (2005).
Polikov et al., "In vitro model of glial scarring around neuroelectrodes chronically implanted in the CNS" Biomaterials, 27(31), pp. 5368-5376. (2006).
Spataro et al., "Dexamethasone treatment reduces astroglia responses to inserted neuroprosthetic devices in rat neocortex" Experimental Neurology 194(2), pp. 289-300. (2005).
Thompson et al., "Interleukin-1 receptor antagonist (IL-1ra) as a probe and as a treatment for IL-1 mediated disease" International Journal of Immunopharmacology,14(3), pp. 475-480. (1992).
Einati, H., et al., Electrochemical studies of self-assembled monolayers using impedance spectroscophy, Electrochimica Acta, 54 (2009) 6063-6069.

\* cited by examiner

- SiO$_2$/Si wafer
- TiN
- S-1818
- Si$_3$N$_4$
- AZ-4262

IL-1 RECEPTOR ANTAGONIST-COATED ELECTRODE AND USES THEREOF

CROSS-REFERENCE TO RELATED APPLICATIONS

This application is the U.S. National Phase under 35. U.S.C. §371 of International Application PCT/IL2012/050266, filed Jul. 23, 2012, which claims the benefit of U.S. Provisional Application No. 61/515,111, filed Aug. 4, 2011 The disclosures of the above-described applications are hereby incorporated by reference in their entirety. The International Application was published under PCT Article 21(2) in English.

TECHNICAL FIELD

The present invention provides an implantable electrode of electrode array designed for brain recording and/or stimulation.

BACKGROUND ART

Implantation of electrodes for electrical deep brain stimulation (DBS) and deep brain recording of neuronal signals are widely used for treatment of brain malfunctions. High frequency electrical DBS is used in cases such as Parkinson's disease (PD), epilepsy, major depression, dystonia and essential tremor. For this, electrodes are implanted in deep brain sites such as the subthalamic nucleus (STN), globus pallidus (GPi) and the pedunculopontine nucleus. Once the electrodes are surgically positioned, no changes can be carried out in their position. Despite the broad research and clinical use, no optimal architecture and placement of the stimulating electrodes was found. It appears that for each individual, the architecture and placement should be optimized separately. For this reason, the number of electrodes and their spatial distribution are critical for the success of the treatment. Additionally, in order to position the electrodes, growing number of surgeons use both magnetic resonance imaging (MRI) and online recordings of the neuronal activity. Such recording is fundamental for positioning the stimulating electrodes, and allow high online spatial resolution during the insertion of the electrode without the dependency in MRI.

Recording of the brain's neuronal activity is also used to interface with peripheral prosthesis as a means for functional rehabilitation of individuals with motor disabilities, to control wheel chairs (Wolpaw and McFarland, 2004), guide computerr cursors (Santhanam et al., 2008) and robotic arms (Abbott, 2006). Multi-electrode arrays (MEAs) are presently used for recording of multichannel neuronal signals mostly from cortical areas of the brain (House et al., 2006; Nicolelis, 2003). A constraining factor of these rehabilitation attempts is the ability to readout a stable and reliable neuronal data. Therefore, the electrode-brain interface needs to withstand the challenge of chronic recording and high signal to noise ratio with minimal effect on the surrounding tissue.

Previous studies reported a decrease in the quality of neuronal signals and the number of functional electrodes in chronic multi-electrode arrays (MEAs) recordings (Polikov et al., 2005). Follow-up studies reported a reduction in the DBS-dependent improvement in motor control in PD patients over time (Wider et al., 2008). Reduced efficacy over time of both recording and stimulation procedures were associated with the brain's immune response, i.e., a glial scar formation, to the chronically implanted electrodes (Nicolelis, 2003; McConnell et al., 2009, Hughes et al., 2011). The glial scar encapsulates the electrode creating a physical barrier between the electrode and the neurons (Polikov et al., 2005; Tate, 2001), and thus, defines a time limit for chronic neuronal recording and stimulation due to the formation of a glial-scar. The current strategy to overcome this problem of biocompatibility of electrode-brain interface is redundancy, thus using a large number, in the range of hundreds, of electrodes, in order to overcome the glial time limit (Nordhausen et al., 1996; Turner et al., 2008). However, while this strategy may be effective for cortical recordings, it is not applicable for deeper brain sites due to the extensive damage it will cause.

Electrode implantation initiates an immune cascade and secretion of immune response regulation factors such as monocyte chemotactic protein-1 (MCP-1) (Babcock et al., 2003), and pro-inflammatory cytokines such as interleukin-1 (IL-1) (Giulian et al., 1994a; 1994b), interleukin-6 (IL-6) (Woodroofe et al., 1991), and tumor necrosis factor (TNF) (Sheng et al., 1995; Chabot et al., 1997) that through a positive feedback loop support the creation of the glial scar (Eng and Ghirnikar, 1994). Histological analysis of the immune response indicated no significant difference in the amount of glial-scarring to different sizes, their surface physical characteristics or the electrode insertion techniques (Polikov et al., 2005; Polikov et al., 2006). Systemic injection of immune suppressors reduced the glial-scar response (Spataro et al., 2005), yet, resulted in severe peripheral metabolic side effects (Kim and Martin, 2006). Several coating agents were tested in order to reduce the level of glial scarring, including alginate hydrogel matrices embedded with dexamethasone (DEX) loaded poly(lactic-co-glycolic acid) (PLGA) nanoparticles (Kim and Martin, 2006). This study showed no increase in the impedance of chronic DEX-coated electrodes, while the impedance of the control electrodes increased by three times within two weeks from implantation, presumably due to the glial scar around the control electrodes. Yet, no electrophysiological or histological data were presented to confirm that the improved impedance stability correlates with improved electrode functionality and biocompatibility. In an additional study, laminin-coated silicon (Si) electrodes were implanted in the rat cortex and brains were examined after one and four weeks for glial scarring (He et al., 2006). Although no difference was found one week after implantation, glial fibrillary acidic protein (GFAP) staining done four weeks after implantation was lower around the laminin-coated electrodes compared to the non-coated control electrodes. This "rescue" effect occurred because the laminin coating passively "camouflaged" the electrode from being identified by the immune system and thus provoked a weaker immune response, indicating that systemic administration of anti-inflammatory agents and electrode protein coatings may serve to minimize glial scarring.

Interleukins (ILs) are cytokines that are known to be scar inducers. In response to brain injury, local inflammatory cells (macrophages) secrete several cytokines, including IL-1, which play a crucial role in the mammalian inflammatory response associated with a wide range of immunologic, metabolic, physiological and hematopoietic activities (Giulian and Tapscott, 1988). The IL-1 family includes three structurally related cytokines, more particularly IL-1α, IL-1β and IL-1 receptor antagonist (IL-1ra), of which IL-1α and IL-1β are pro-inflammatory agonists while IL-1ra blocks IL-1α and IL-1β activity (Morgan et al., 2004; Thompson et al., 1992). All known functions of IL-1 family are mediated via the IL-1 receptor. Systemic administration of IL-1ra was found to effectively inhibit glial-scar development at injury sites (Bendele et al., 2000; Born et al., 2000).

US 2005/0149157 discloses, inter alia, a medical device for various therapeutic indications, said device comprising an electrical device such as an electrode and an anti-scarring agent selected from various categories of agents, e.g., cell cycle inhibitors, wherein the anti-scarring agent inhibits scarring between the device and the host into which the device is implanted. The anti-scarring agent may either coat the device or, alternatively, locally administered to the implantation site.

SUMMARY OF INVENTION

It has now been found, in accordance with the present invention, that coating electrodes with the IL-1 antagonist interleukin-1 receptor antagonist (IL-1ra) actively and significantly limits, i.e., inhibits or reduces, local scarring on or around the surface of said electrodes when chronically implanted into a brain, without the side effects resulting from systemic administration of an IL-1 antagonist. Furthermore, glial scarring observed around IL1-ra-coated electrode insertion site several weeks after implantation was significantly lower than that observed following laminin-coated electrode implantation. Such biocompatible IL1-ra-coated electrodes may thus allow long lasting high quality stimulation and/or recording of brain areas in general and deep brain areas in particular.

In one aspect, the present invention thus provides an electrode designed for implantation into the central nervous system (CNS) of a mammal, said electrode being substantially coated with interleukin-1 receptor antagonist (IL-1ra) or a coating composition comprising it, wherein the IL-1ra actively inhibits scarring on or around the surface of said electrode when implanted into the CNS.

The electrode of the present invention may be either active, i.e., comprising an on-chip amplification and/or buffering for amplifying and/or buffering recorded signals, or passive, and may be configured in any suitable configuration, e.g., as a single-channel electrode or a multi-channel electrode optionally configured as an implantable multi electrode array (MEA). It should further be noted that this electrode may be either a single-shank electrode or a member of a vector electrode or a three-dimensional (3D) electrode as described, e.g., in Aziz et al. (2009).

In another aspect, the present invention provides a coating composition comprising IL-1ra for use in inhibiting scarring on or around the surface of an electrode when implanted into the CNS of a mammal.

In still another aspect, the present invention relates to IL-1ra for use in inhibiting scarring on or around the surface of an electrode when implanted into the CNS of a mammal.

In a further aspect, the present invention relates to a method for CNS recording and/or CNS stimulation in an individual suffering from a CNS dysfunction, disease or disorder, or CNS injury, said method comprising the step of implanting into the CNS of said individual at least one electrode substantially coated with IL-1ra or a coating composition comprising it, wherein the IL-1ra actively inhibits scarring on or around the surface of said at least one electrode.

DETAILED DESCRIPTION OF THE INVENTION

As stated above, a growing body of research and therapeutic techniques in the fields of deep brain stimulation (DBS) and brain computer interface (BCI) use silicon-based multi-channel electrodes to acquire neuronal signals and deliver localized electrical stimulation to the brain. Yet, the ability to record and stimulate is compromised by the development of a physical barrier, i.e., glial scar, between the electrode and the brain tissue. Previous studies have demonstrated that glial scarring can be limited in subjects under systemic administration of immune suppressors; however, such administration results in dangerous side effects due to systemic immune suppression. Other studies used inert proteins such as laminin to passively "camouflage" the electrodes implanted from being identified by the immune system.

The study underlying the present invention demonstrates a novel approach for actively and significantly inhibiting the immune response of the central nervous system (CNS), more particularly the brain, to an implanted electrode, by coating said electrode with a bioactive protein, more specifically interleukin-1 receptor antagonist (IL-1ra).

In one aspect, the present invention provides an electrode designed for implantation into the CNS of a mammal, said electrode being substantially coated with IL-1ra or a coating composition comprising it, wherein the IL-1ra actively inhibits scarring on or around the surface of said electrode when implanted into the CNS.

The term "mammal" as used herein refers to a human as well as to any other mammalian such as, without being limited to, a non-human primate, e.g., a monkey or ape, a mouse, a rat, a dog, a cat, a horse, or a cow. In preferred embodiments, the mammal according to the present invention is a human.

When electrodes are implanted in the CNS they are subject to a "foreign body" response from the surrounding host tissues. The body recognizes the implanted electrode as foreign, which triggers an inflammatory response followed by encapsulation of the implant with glial tissue, a process called "gliosis". The term "scarring" or "gliosis", as used herein, refers to the formation of scars, i.e., scar tissue, by glial astrocytes in response to implantation of a foreign body such as an electrode into the CNS. When scarring occurs around an implanted electrode, the electrical characteristics of the electrode-tissue interface degrade, and the device fails to function properly. In such cases, the reduced resistance imposed by the intervening glial tissue damages the specificity and thus the efficacy of the DBS, and additional electrical current from the lead is necessary. This may consequently shorten the battery life of the implant, prevent electrical conduction altogether rendering the electrode clinically ineffective, and/or cause damage to the CNS tissue. Furthermore, the surrounding tissue may be inadvertently damaged from the inflammatory foreign body response, which can result in loss of function or tissue necrosis.

The term "interleukin-1 receptor antagonist", or "IL-1ra", as used herein interchangeably, refers to a protein member of the IL-1 cytokine family encoded in human by the IL1RN gene, which binds to the cell surface interleukin-1 receptor (IL-1R) thus inhibiting the activities of IL-1α and IL-1β, and consequently preventing IL-1 from sending a signal to that cell; and further modulating a variety of IL-1 related immune and inflammatory responses. A recombinant non-glycosylated version of human IL-1ra is available under the brand name Kineret® (anakinra) and indicated for the reduction in signs and symptoms and slowing the progression of structural damage in moderately to severely active rheumatoid arthritis, in adults who have failed one or more disease-modifying antirheumatic drugs (DMARDs). As shown herein, this protein actively inhibits the creation of the immune cascade in the brain thus significantly limits the formation of the immune-dependent barrier, i.e., glial-scar, on or around the surface of electrodes coated therewith, when chronically implanted into the brain.

The terms "inhibit scarring", "inhibit gliosis", "reduce gliosis" and "limit the formation of glial-scar", used herein interchangeably, refer to the action of IL-1ra or a composition comprising it, when coating an electrode implanted into the CNS of a mammal, which results in a statistically significant decrease in the formation of glial tissue, i.e., scar tissue, on or around the surface of said electrode. The remarkable decrease in the amount of glial tissue formed during chronic implantation of the electrode allows long lasting and continuous high quality functioning of said electrode.

The term "implanted into the CNS" means that the implantable electrode is completely or partially placed within the CNS. An electrode is partially implanted when some of the electrode reaches, or extends to, the outside of the host, i.e., the mammal. Implantable electrodes such as the electrodes of the present invention may be implanted into the CNS, more particularly the brain, for treatment of different medical conditions and for various time periods. Nevertheless, treatment of most of those conditions is usually associated with chronic implantation of the electrode(s).

The electrode of the present invention is substantially coated with either IL-1ra or a biocompatible coating composition comprising it. The term "substantially coated" means that the electrode is not necessarily completely coated with IL-1ra or said composition. In fact, the surface of the electrode, which should be coated according to the present invention, is the part which is practically inserted into the CNS tissue and has a direct contact thereto only. Moreover, in order to enable satisfactory signal transmission from and to the CNS tissue, it is possible that the surface of the conducting leads, i.e., the points of contact between the electrical leads and the CNS tissue, will be partially coated with IL-1ra or said composition. The amount of coverage of the IL-1ra will depend on the application parameters, i.e., time of use, exposure, level of signals, levels of noise, etc. While inert proteins such as laminin-based coating passively "camouflage" the alien electrode from being identified by the immune system and thus initiate less long-term immune reaction, the IL-1ra coating further actively inhibits the creation of the immune cascade in the CNS thus remarkably limits the formation of glial scar on or around the surface of the electrode, and consequently insuring the functionality of the electrode over time.

The electrode of the present invention may be either active, when having on-chip amplification and/or buffering for amplifying and/or buffering recorded signals, or passive, and may be configured as a single-channel electrode or a multi-channel electrode, but it is preferably a multi-channel electrode.

The terms "single-channel electrode" and "multi-channel electrode" as used herein refer to electrodes comprising a sole electrical lead or multiple, e.g., 2-36, electrical leads, respectively. The term "electrical lead", as used herein, refers to a wire or other material capable of transmitting electrical impulses, which is used as a conductor in the electrode of the present invention to carry, i.e., transmit, electrical signals, more specifically, to acquire neuronal signals and deliver localized electrical stimulation from and to the CNS, respectively. The electrode of the present invention, either a single- or multi-channel electrode, may be of any suitable configuration known in the art. For example, a single-channel electrode may comprise an electrical lead encased in a coating material; and a multi-channel electrode may comprise multiple electrical leads, wherein each one of said electrical leads is encased in a coating material, or said electrical leads are imprinted on a carrier and coated with a coating material, thus forming an implantable multi electrode array (MEA).

Preferred electrodes according to the present invention, particularly when designed for brain recording and/or stimulation, are multi-channel electrodes, preferably configured as implantable MEAs, having a long shaft that allows the insertion and positioning of the electrode in deep brain structures, and low biological signature that induces, upon implantation into the CNS, low level of immune reaction thus enables minimal impact on the CNS tissue, i.e., minimal short- and long-term damage, and minimal interruption with the normal functionality of the CNS tissue.

The electrical leads comprised within the electrode of the present invention may be made of any conductive material suitable for acquiring neuronal signals and delivering electrical stimulation from and to the CNS, in particular, from and to the brain.

In certain embodiments, the electrical leads comprised within the electrode of the invention are made of a metal, preferably a noble metal such as gold, platinum, iridium, osmium, silver, palladium, rhodium or ruthenium. Examples of non-noble metals include, without being limited to, mercury, polonium, copper, bismuth, technetium, rhenium, and antimony.

In other embodiments, the electrical leads comprised within the electrode of the invention are made of a metal alloy. Non-limiting examples of suitable metal alloys include nitrides of refractory metals, e.g., TiN and TaN, metal borides, metal carbides, metal silicides, beryllides, metal selenides, metal phosphides, metal chromides, mixtures of the aforesaid, ternary alloys of the aforesaid with other elements such as TaSiN, TiCN and TiAlN, non-toxic nickel alloys such as NiTi, and quaternary mixtures such as TiTaSiN.

In further embodiments, the electrical leads comprised within the electrode of the invention are made of a metalloid such as, without being limited to, boron, silicon, germanium, arsenic, antimony, tellurium, or polonium.

In still other embodiments, the electrical leads comprised within the electrode of the invention are made of a conducting ceramic material having metallic properties. Examples of conducting ceramic materials having metallic properties include, without being limited to, metal nitrides such as titanium nitride and alumina nitride, metal carbides, metal borides such as titanium diboride, metal silicides, metal beryllides, metal selenides, metal phosphides, metal chromates, metal-silicon nitrides such as TaSiN and TiSiN, metal-silicon carbides such as TaSiC, metal-silicon borides such as TiSiB, or mixtures thereof.

The coating material coating the electrical leads of the electrode of the invention, as well as the carrier onto which, in particular electrode configurations, the electrical leads are imprinted, are insulators forming a passivation layer coating said electrical leads. These insulators may be made of any material suitable for implantation into an organ of a mammal, particularly a human, such as silicon-based insulators, e.g., silicon nitride, silicon dioxide and silicon oxynitride; metal oxides, i.e., non-silicon-based insulators, e.g., aluminum oxide, tantalum oxide and hafnium oxide; and polymers, e.g., a polyimide or a plastic obtained following polymerization of either natural or synthetic organic monomers. Polyimides are polymers of imide monomers which, according to the composition of their main chain, may be aliphatic, i.e., linear, semi-aromatic, or aromatic polyimides. Examples of such imide monomers include, without being limited to, pyromellitic dianhydride and 4,4'-oxydianiline. The term polyimide further refers to polyetherimides and analogous polyimides having other linkages, e.g., sulfones, replacing the oxygen linkages in the polyetherimides, as well as to polymer blends containing one or more kinds of imide units; copolymers containing one or more kinds of imide units; graft polymers, i.e., branched polymers having side chains composed of monomers different than that of the main chain, containing one or more kinds of imide units; and imidizable polymers which are only partially imidized. Non-limiting examples of specific polyimides include polyglutarimide, polymaleimide, polyitaconimide, as well as commercially available polyimides such as poly(4,40-oxy-diphenylene-pyromellitimide) (PMDA-ODA tradename: Kapton, DuPont), biphenyltetra carboxylic dianhydride/para-phenylenediamine (BPDAPPD, tradename: U-Varnish-S (UBE) or PI2611 (HD-MicroSystems)), or Durimide 7510 (Fuji film) comprising at least 50-70% N-methyl-2-pyrrolidonene, 25-40% polyamid acid esters, 4-6% methacrylate monomers, and 0.8-1.5% of an organotitanium complex. Plastic materials that can be used as insulators include both thermoplastics such as, without limiting, polyethylene, polypropylene, polystyrene, polyvinyl chloride, polyvinyl difluoride (PVDF), and polytetrafluoroethylele (PTFE), as well as thermosetting polymers such as, without limiting, epoxy-based coatings (e.g., SU8), novolac (phenol formaldehyde)-based resins such as photoresists, and polyimides.

In particular embodiments, the electrode of the present invention is an IL-1ra-coated multi-channel electrode as defined above, e.g., a 4-, 5-, 6-, 7-, 8-, 9-, 10-, 11-, 12-, 13-, 14-, 15-, 16-, 17-, 18-, 19-, or 20-channel electrode. In more particular embodiments, this electrode is configured as an implantable MEA, having a long shaft allowing flexibility in the number, position and ensemble of the recording/stimulating electrical leads with both passive and active reduced immune reactivity that ensure the functionality of the electrode over time.

Figure 1:
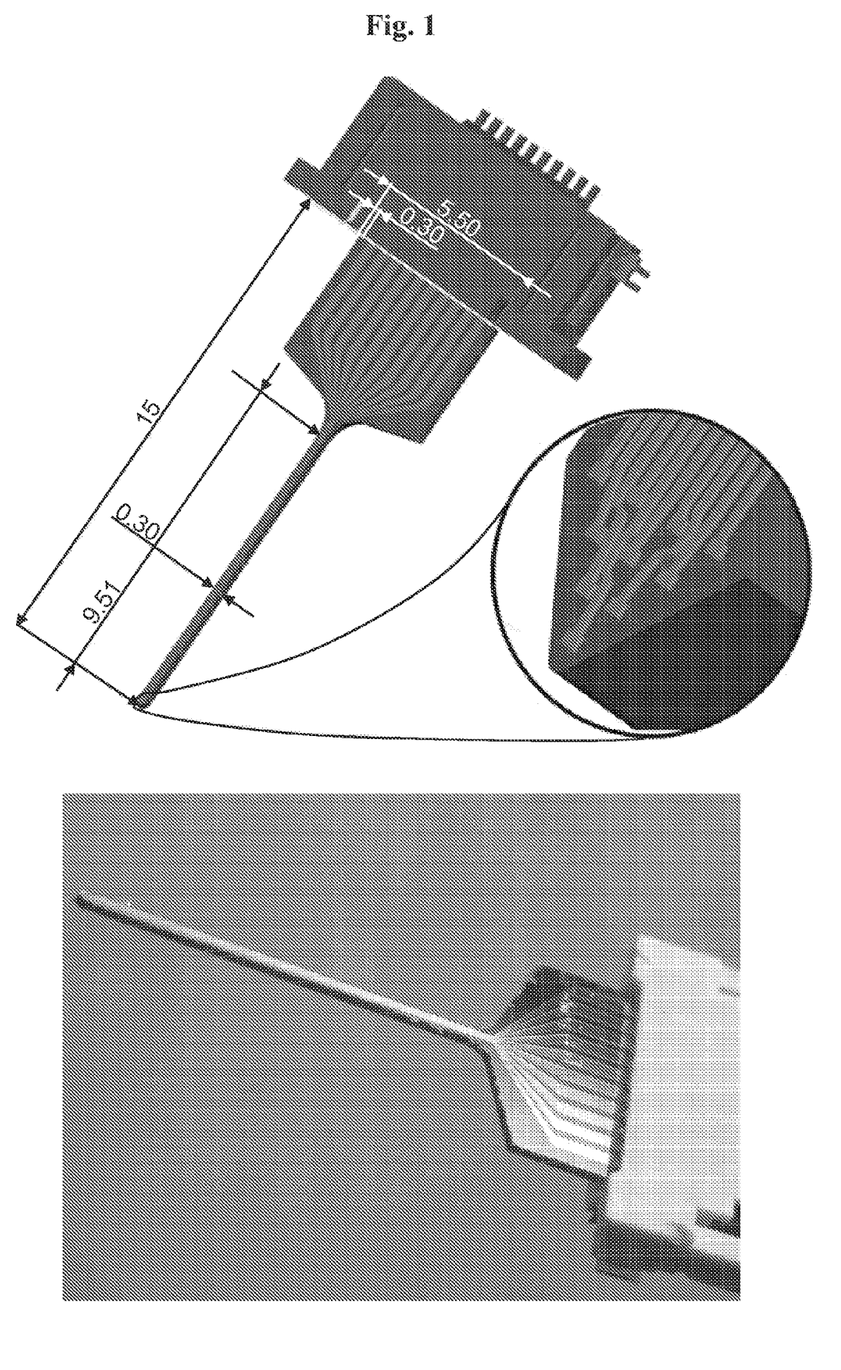
FIG. 1 shows the layout of a particular single-shank multi-channel electrode configured as an MEA, as used in the study described herein, comprising 10 electrical leads arranged on a penetrating tip, wherein said leads are made of titanium-nitride (TiN; 300 Å), imprinted on silicon nitride ($Si_3N_4$; 150 Å) and coated with silicon nitride ($Si_3N_4$; 150 Å) (upper panel); and its installation as performed in electrophysiological tests (lower panel). Measures in the figure are given in mm.
Figure 2:
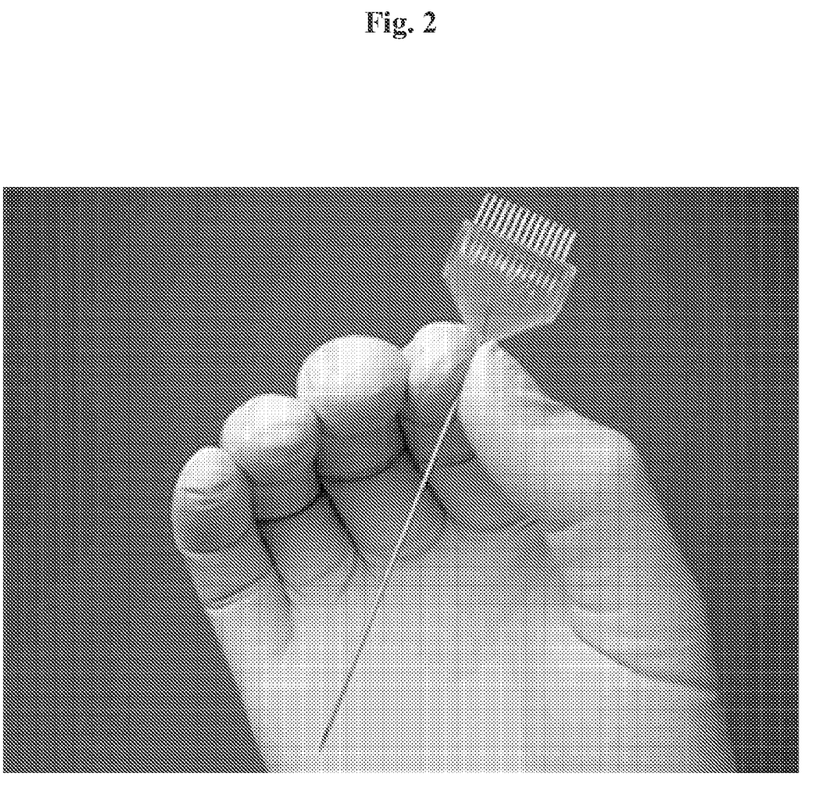
FIG. 2 shows a particular single-shank multi-channel electrode configured as an MEA and presented in http://www.medtrode.com/products/electrodes.htm, comprising 14 electrical leads arranged on a penetrating tip, wherein said leads are made of noble metal such as platinum, imprinted on and coated with a polyimide.

In one specific embodiment, the electrode of the invention is a single-shank multi-channel electrode configured as an implantable MEA as used in the study described herein and shown in FIG. 1, comprising 10 electrical leads arranged on a penetrating tip, wherein said leads are made of a conductive ceramic material such as titanium-nitride (TiN; 300 Å), imprinted on silicon nitride ($Si_3N_4$, 150 Å) as a carrier and coated with silicon nitride ($Si_3N_4$, 150 Å) as a coating material. Due to the morphology and texture of the specific TiN layer, the surface of each one of the leads in this particular electrode is rough thus providing increased effective conducting area. In another specific embodiment, the electrode of the invention is a single-shank multi-channel electrode configured as an implantable MEA as shown in http://www.medtrode.com/products/electrodes.htm and in FIG. 2, comprising 14 electrical leads arranged on a penetrating tip, wherein said leads are made of a noble metal such as platinum, imprinted on and coated with a polyimide.

In certain embodiments, the electrode of the present invention is a single-shank single-channel- or multi-channel electrode as defined above. Particular such electrodes are single-shank multi-channel electrodes configured as implantable MEAs, e.g., the single-shank MEA used in the study described herein and shown in FIG. 1, or the single-shank MEA shown in FIG. 2. In other embodiments, the electrode of the invention is a member of a vector electrode or a 3D-electrode as described, e.g., in Aziz et al. (2009).

In certain embodiments, the electrode of the present invention, in any one of the configurations defined above, is specifically designed for implantation into a brain of a mammal, preferably a human. In one particular embodiment, the electrode of the invention is designed for brain recording, more particularly, deep brain recording. In another particular embodiment, the electrode of the invention is designed for brain stimulation, more particularly, deep brain stimulation. In a further particular embodiment, the electrode of the invention is designed for both brain recording and brain stimulation, more particularly, both deep brain recording and stimulation.

The coating of the electrode of the present invention with IL-1ra may be performed utilizing any technology known in the art, e.g., as described in Einati et al. (2009) and exemplified in the study described herein, wherein the coating process depends on the insulator forming the passivation layer coating the electrical leads of the electrode, and comprises the assembling of either one or two adhesive layers herein identified upper- and lower-adhesive layers.

According to the present invention, the upper-adhesive layer comprises a compound capable of covalently linking to an amino group of IL-1ra and to either the insulator forming the passivation layer or a functional group of a compound composing the lower-adhesive layer; and the lower-adhesive layer, if present, comprises a compound capable of covalently linking to the insulator forming the passivation layer and to a functional group of a compound composing the upper-adhesive layer. In other words, the IL-1ra layer coat is formed by covalently linking said protein via one or more amino groups thereof to an upper adhesive layer, which is covalently linked to the surface of the passivation layer of the electrode, or alternatively, to a lower-adhesive layer linked to the surface of said passivation layer. Nevertheless, in order to ensure a homogeneous monolayer of IL-1ra coating, in certain cases both upper- and lower-adhesive layers may be assembled onto the surface of the passivation layer even if the compound composing the upper-adhesive layer is capable of covalently linking to the insulator composing the passivation layer and a lower-adhesive layer is thus not necessarily required.

Examples of compounds that may be used for assembling the upper-adhesive layer include, without being limited to, succinaldehyde, glutaraldehyde, adipaldehyde, heptanedial, and octanedial. Additional examples of such compounds include cyanoacrylate type adhesives, e.g., Aron Alpha A (Toagosei Co., Ltd., Japan) and Biobond (Yoshitomi Pharmaceutical Industries, Ltd., Japan); fibrin glues, e.g., Tisseel (Nippon Zoki Pharmaceutical, Osaka, Japan), Beriplast (Hoechst), and Bolheal (Chemo-Sero-Therapeutic Research Institute, Kumamoto, Japan); gelatin-resorcin—(bifunctional or multifunctional) aldehyde type adhesives, e.g., Cardial GRP Glue (Cardial, France, described in Otani et al., 1996); and polyelectrolyte multilayers of hyaluronic acid and chitosan, coupled with surface-immobilized cell-adhesive arginine-glycine-aspartic acid (RGD) peptide (Chua et al., 2008).

Non-limiting examples of compounds that may be used for assembling a lower-adhesive layer include amino functional alkoxysilanes of the formula $H_2N-(C_1-C_8)$alkylene-$Si(OR_1)_3$ or $H_2N(C_1-C_8)$alkylene-$SiR_2(OR_1)_2$, or mercapto functional alkoxysilanes of the formula $HS-(C_1-C_8)$alkylene-$Si(OR_1)_3$ or $HS-(C_1-C_8)$alkylene-$SiR_2(OR_1)_2$, wherein $R_1$ each independently is $(C_1-C_4)$alkyl, preferably, methyl, ethyl or propyl; and $R_2$ each independently is $(C_1-C_4)$alkyl or H, such as 4-aminobutyltrimethoxysilane, 4-aminobutyldimethoxysilane, 4-aminobutylmethoxy silane, 4-aminobutyltriethoxysilane, 4-aminobutyldiethoxysilane, 4-aminobutyl ethoxysilane, 3-aminopropyltrimethoxysilane (APTMS), 3-aminopropyldimethoxy silane, 3-aminopropylmethoxysilane, 3-aminopropyltriethoxysilane, 3-aminopropyl diethoxysilane, 3-aminopropylethoxysilane, 2-aminoethyltrimethoxysilane, 2-aminoethyldimethoxysilane, 2-aminoethylmethoxysilane, aminopropylmethyl dimethoxysilane, aminopropylmethyl diethoxysilane, 4-mercaptobutyltrimethoxy silane, 4-mercaptobutyldimethoxysilane, 4-mercaptobutylmethoxysilane, 4-mercaptobutyltriethoxysilane, 4-mercaptobutyldiethoxysilane, 4-mercaptobutyl ethoxysilane, 3-mercaptopropyltrimethoxysilane, 3-mercaptopropyldim ethoxy silane, 3-mercaptopropylmethoxysilane, 3-mercaptopropyltriethoxysilane, 3-mercaptopropyldiethoxysilane, 3-mercaptopropylethoxysilane, 2-mercaptoethyl trimethoxysilane, 2-mercaptoethyldimethoxysilane, 2-mercaptoethylmethoxysilane, mercaptopropylmethyl dimethoxysilane, and mercaptopropylmethyl diethoxysilane. Additional compounds that may be used for assembling a lower-adhesive layer include aminoalkanethiols such as of the formula $H_2N-(C_1-C_8)$alkylene-SH; carboxyalkanethiols such as of the formula $HOOC-(C_1-C_8)$alkylene-SH; hydroxyalkanethiols such as of the formula $HO-(C_1-C_8)$alkylene-SH; carboxyalkyldisulfide such as of the formula $HOOC-(C_1-C_8)$alkylene-S—S—$(C_1-C_8)$alkylene-COOH; succinimidyl esters such as dithiobis(succinimidyl butanate), dithiobis(succinimidyl hexanate), dithiobis(succinimidyl octanate), and dithiobis(succinimidyl undecanate); and ferrocenylalkanethiols such as of the formula ferrocenyl-$(C_1-C_8)$alkylene-SH.

In a particular embodiment described herein, the passivation layer is made of silicon nitride ($Si_3N_4$), on top of which a lower-adhesive layer made of APTMS and an upper-adhesive layer made of glutaraldehyde are assembled, wherein a first carbonyl of the glutaraldehyde is linked to an amino group of IL-1ra and a second carbonyl group of the glutaraldehyde is linked to the amino group of APTMS that is further linked via silicon-oxide or silicon-nitrogen bonds to the silicon nitride composing the passivation layer.

Upon completion of the coating process, a homogeneous layer, preferably monolayer, of the anti-scarring agent is obtained all over the treated surface of the electrode. Nevertheless, upon transferring of an electrical current through the coated electrode, before or after implantation into the CNS, either part of or the entire anti-scarring agent coating the surface of the electrical leads is released from the non-passivated areas of the leads, if left. In any case, it is assumed that a partial coating of the surface of the electrical leads will not reduce the signal transmission efficacy of the electrode and may even improve it due to the interactions formed between the protein coating and the CNS tissue.

In the study described in the Examples section hereinafter, burr-holes were made bilaterally at 0.2 mm anterior and 3.0 mm lateral to the bregma of Sprague-Dawley rats, and electrodes were implanted using standard stereotaxic methods to 8.5 mm ventral to bregma. Some of the animals were implanted with IL1-ra-coated electrode and non-coated electrode, one in each hemisphere, and the other animals were implanted with IL1-ra-coated electrode and laminin-coated electrode, one in each hemisphere. After stereotaxic insertion, electrodes were fixed to the skull using dental acrylic and stainless steel screws, and the skin was sutured anterior and posterior to the acrylic construction. Either one or four weeks after electrodes implantation, rats were deeply anaesthetized, brains were extracted and post-fixed in 1% fresh paraformaldehyde, and three successive 30-μm thick horizontal sections were cut through the cortex and stained so as to examine glial fibrillary acidic protein (GFAP) area, measured as integrated optical density (IOD). As shown, whereas extensive scarring could be observed for the non-coated electrodes, at four weeks post implantation, the GFAP stained area at up to 100 μm in radius around the IL-1ra-coated electrode lesion was significantly lower than that around both the non-coated electrode and surprisingly also the laminin-coated electrode, and in fact, did not significantly differ from intact brain tissue far away from the electrode insertion site.

The results presented herein show significantly lower GFAP staining in the tissue surrounding the IL-1ra-coated electrodes vs. non-coated Si electrodes and laminin-coated electrodes. Both astroglia and microglia take part in the brain immune reaction to electrode implantation. Yet, microglial count was increased only during early stages after implantation and returned to baseline levels, while "increased astroglial count was readily visible 3 years after Implantation" (Griffith and Humphrey, 2006). GFAP staining is a well-accepted method for the assessment of astroglial scarring due to chronic implantation of Si electrodes (Polikov et al., 2005; Eng et al., 2000). A growing body of research and therapeutic techniques in the fields of deep brain stimulation and brain computer interfaces utilized Si multi-channel electrodes to acquire neuronal signals and deliver localized electrical stimulation to the brain. Yet, the ability to record and stimulate is compromised by the development of a physical barrier i.e. a glial scar, between the electrode and the brain tissue. Past studies have demonstrated that glial scarring may be reduced by systemic administration of immune suppressors. Yet such systemic administration results in dangerous side effects due to systemic immune suppression (Spataro et al., 2005; Kim and Martin, 2006). Alternatively, researchers have tried to "camouflage" the electrodes using inert proteins such as laminin (Giulian and Tapscott, 1988) and demonstrated a lower immune response vs. that seen with non-coated electrodes, which is likely due to passive processes. The present study demonstrates a novel approach for lowering the brain's immune response to electrodes, e.g., Si electrodes, by coating them with an active immune suppressing protein. The results presented herein showed a local reduction in the level of glial scarring around IL-1ra-coated electrode compared to that observed around non-coated Si electrodes. Interestingly, unlike studies that used passive electrode coating such as laminin, IL-1ra coated electrodes induced less GFAP staining vs. non-coated electrodes already in the one week group and induced less GFAP staining compared to laminin coated electrodes in the four weeks group. The present results strongly suggest that an active immune suppressing protein, if applied locally, reduces the level of the immune response to chronically implanted electrodes already one week after implantation and performs better than passive protein coating four weeks after implantation. In particular, IL-1ra-coated biocompatible electrodes may allow long lasting and continuous high quality stimulation and recording of deep brain areas, and therefore can be used for both research and therapeutic applications.

In certain particular embodiments, the electrode of the present invention, either passive or active, in any one of the configurations defined above, is used for treatment of a brain dysfunction or a brain disease or disorder.

Brain dysfunction, resulting from a brain damage, may range from complete loss of motor, emotional and cognitive functions such as the case in coma, to localized and specific decrease in the above functions below normal level, such as orientation and attention deficits in delirium, to impairment of one or several of the many specific functions that contribute to motor, emotional and cognitive functions and behavior. The type and severity of brain dysfunction depend on how extensive brain damage is, where the damage is, and how quickly the cause of the damage is progressing. Brain dysfunction may be widespread, i.e., diffused, or limited to a specific area, i.e., localized.

Diffuse brain dysfunction is caused by brain damage that affects large areas of the brain, including disorders that cause metabolic abnormalities, such as control of levels of sugar in the blood (hypo- and hyper-glycemia) or low levels of oxygen in the blood (usually due to a lung, heart or blood vessels disorder); infections, such as meningitis and encephalitis; and either very high or low blood pressure. Diffuse brain dysfunction may further result from disorders that cause swelling of or put pressure on a large area of the brain, including brain abscesses; large brain tumors; and severe or blunt head injuries. Certain drugs such as opioids (narcotics), some sedatives, e.g., benzodiazepines and barbiturates, and antidepressants, may cause diffuse brain dysfunction if people are sensitive to their effects (as older people are) or if the level of drug in the blood is too high.

Localized brain dysfunction is caused by disorders that affect a specific area of the brain, including brain tumors that affect a relatively small area of the brain; disorders that reduce the blood flow, and thus the oxygen supply to a specific area, such as a stroke; penetrating head injuries that affect a relatively small area of the brain; and certain types of seizure disorders.

While diffuse brain damage tends to affect consciousness, making people either difficult or impossible to arouse, localized brain damage tends to affect specific functions. Nevertheless, the severity of brain dysfunction depends on both the extent of brain damage and the location. When the cerebral cortex, i.e., the outer layer of the cerebrum, is damaged, the degree of dysfunction in most cases is proportional to the extent of the damage, wherein the more extensive the damage, the more severe the dysfunction is likely to be. However, when the brain stem, which regulates critical body functions such as respiration, blood pressure, sleeping, etc., and levels of consciousness, is damaged, a relatively small amount of damage may cause complete loss of consciousness and even death.

The electrode of the present invention can be used for treatment of any type and severity of a brain dysfunction, either widespread or limited to a specific area as defined above.

In certain specific embodiments, the electrode of the invention is used for treatment of a brain dysfunction associated with an autoimmune disease.

In other specific embodiments, the electrode of the invention is used for treatment of a brain dysfunction associated with head trauma or neuronal trauma.

In further specific embodiments, the electrode of the invention is used for treatment of chronic pain or phantom limb pain, resulting from brain dysfunction.

In yet other specific embodiments, the electrode of the invention is used for treatment of a brain disease or disorder selected from Parkinson's disease, epilepsy, dystonia, essential tremor, Tourette syndrome, a mental disorder such as major depressive disorder also known as major depression, or an anxiety disorder such as obsessive-compulsive disorder.

In still other specific embodiments, the electrode of the invention is used for treatment of a brain disease or disorder associated with brain degradation or age-related brain degeneration.

In other particular embodiments, the electrode of the present invention, either passive or active, in any one of the configurations defined above, is used for treatment of a brain injury such as traumatic brain injury, also known as intracranial injury, which occurs when an external force traumatically injures the brain.

A brain-computer interface (BCI), also known as a direct neural interface or a brain-machine interface (BMI), is a direct communication pathway between the brain and an external device, often aimed at assisting, augmenting or repairing human cognitive or sensory-motor functions. Since research and development of BCIs has began on the 1970s, this field has been primarily focused on neuroprosthetics applications that are aimed at restoring damaged hearing, sight, movement, ability to communicate, and even cognitive function. The differences between BCIs and neuroprosthetics, an area of neuroscience concerned with neural prostheses, are mostly in the ways the terms are used. In particular, while neuroprosthetics typically connect the nervous system, either the central or peripheral nervous system, to a device, BCIs usually connect the CNS, more particularly the brain, with a computer system. Nevertheless, both BCIs and neuroprosthetics use similar experimental methods and surgical techniques.

Invasive BCI research in human has targeted repairing damaged sight and providing new functionality to persons with paralysis. Invasive BCIs are implanted directly into the grey matter of the brain during neurosurgery. As they rest in the grey matter, invasive devices produce the highest quality signals of BCI devices but are prone to scar-tissue build-up, causing the signal to become weaker or even lost as the body reacts to a foreign object in the brain. Partially invasive BCI devices are implanted inside the skull but rest outside the brain rather than within the grey matter. They produce better resolution signals than non-invasive BCIs where the bone tissue of the cranium deflects and deforms signals and have a lower risk of forming scar-tissue in the brain than fully-invasive BCIs. A further technology related to BCI which has been tested uses non-invasive neuroimaging as interfaces, wherein signals recorded in this way have been used to power muscle implants and restore partial movement in an experimental volunteer. Although they are easy to wear, non-invasive implants produce poor signal resolution because the skull dampens signals, dispersing and blurring the electromagnetic waves created by the neurons. Although the waves can still be detected it is more difficult to determine the area of the brain that created them or the actions of individual neurons.

In further particular embodiments, the electrode of the present invention, either passive or active, in any one of the configurations defined above, is thus used for brain computer interface or brain machine interface.

Electrotherapy is the use of electrical energy as a medical treatment, e.g., the use of electrical devices such as deep brain stimulators for treatment of a neurological disease. This term has also been specifically applied to the use of electric current to speed wound healing as well as to a range of alternative medical devices and treatments. In particular, electrotherapy is now used for relaxation of muscle spasms, prevention and retardation of disuse atrophy, increase of local blood circulation, muscle rehabilitation and re-education electrical muscle stimulation, maintaining and increasing range of motion, management of chronic and intractable pain, post-traumatic acute pain, post-surgical acute pain, immediate post-surgical stimulation of muscles to prevent venous thrombosis, wound healing and drug delivery.

In still further particular embodiments, the electrode of the present invention, in any one of the configurations defined above, is thus used for brain electrotherapy.

In another aspect, the present invention thus provides a coating composition comprising IL-1ra for use in inhibiting scarring on or around the surface of an electrode when implanted into the CNS of a mammal.

The coating composition of the present invention is biocompatible, i.e., physiologically acceptable, and insoluble, i.e., poorly or very poorly soluble, in aqueous solution under physiological conditions. The insolubility of the composition is of high importance so as to guarantee that the anti-scarring agent, i.e., the IL-1ra, is not released from the composition, and that the concentration of the anti-scarring agent in the composition does not substantially decrease during time.

In one embodiment, the coating composition is used for coating an electrode designed for implantation into the CNS of a mammal, more particularly, into the brain of said mammal. Such electrodes may be either passive or active, and configured as either single- or multi-channel electrodes having any suitable configuration as defined above, for chronic implantation into a brain. In a particular embodiment, the electrode coated with the coating composition of the invention is a multi-channel electrode, optionally configured as an implantable MEA, having a long shaft and low biological signature as defined above. The electrode coated with the coating composition of the invention may be either a single-shank electrode or a member of a vector electrode or a 3D electrode.

In certain embodiments, the coating composition of the invention is used for inhibiting scarring on or around the surface of an electrode having any configuration known in the art, e.g., a multi-channel electrode configured as an implantable MEA, when implanted into the brain for brain recording, more particularly deep brain recording; brain stimulation, more particularly deep brain stimulation; or both brain recording and brain stimulation, more particularly both deep brain recording and stimulation. In particular embodiments, the coating composition of the invention is used for coating electrodes for treatment of a brain dysfunction, a brain disease or disorder, or a brain injury, as defined above.

In still another aspect, the present invention relates to IL-1ra for use in inhibiting scarring on or around the surface of an electrode when implanted into the CNS of a mammal.

In a further aspect, the present invention relates to a method for CNS recording and/or CNS stimulation in an individual suffering from a CNS dysfunction, disease or disorder, or CNS injury, said method comprising the step of implanting into the CNS of said individual at least one electrode substantially coated with IL-1ra or a coating composition comprising it, wherein the IL-1ra actively inhibits scarring on or around the surface of said at least one electrode. The method of the present invention can be used for CNS recording, CNS stimulation, or both CNS recording and stimulation. In particular embodiments, the method of the invention is used for brain recording, more particularly deep brain recording, brain stimulation, more particularly deep brain stimulation, or both brain recording and stimulation, more particularly deep brain recording and stimulation.

Each one of said at least one electrode implanted into the CNS of the individual according to the method of the present invention may independently be passive or active, and configured as either a single- or a multi-channel electrode as defined above. In particular embodiments, at least one of said at least one electrode implanted into the CNS, or each one of said at least one electrode implanted into the CNS, is a multi-channel electrode, preferably configured as an implantable MEA, having a long shaft and low biological signature.

The method of the present invention comprises the step of implanting into the CNS of the individual treated at least one electrode substantially coated with IL-1ra or a coating composition comprising it, wherein the IL-1ra actively inhibits, i.e., limits, scarring on or around the surface of said at least one electrode. In certain embodiments, the method of the invention comprises the step of implantation of a sole such electrode that is either a single-channel electrode or a multi-channel electrode optionally configured as an implantable MEA. In other embodiments, the method comprises the step of implantation of a plurality of electrodes, wherein each one of the electrodes independently is a single-channel electrode or a multi-channel electrode optionally configured as an implantable MEA.

According to the method of the present invention, each one of said at least one electrodes implanted into the CNS is independently either a single-shank electrode, or a member of a vector electrode or a 3D electrode.

The method of the present invention is aimed at CNS recording and/or stimulation, more particularly, chronic CNS recording and/or stimulation, in an individual suffering from a CNS dysfunction, disease or disorder, or CNS injury, as defined above. In particular embodiments, this method is aimed at brain recording, more particularly deep brain recording, and/or brain stimulation, more particularly deep brain stimulation, wherein the IL-1ra or the composition coating each one of electrodes inhibits scarring on or around the surface of each one of said electrodes following implantation into the brain.

The method of the invention may be used for inhibiting scarring on or around the surface of an electrode implanted into the brain so as to treat a brain dysfunction; a brain disease or disorder; or a brain injury, as defined above. The method may further be used for inhibiting scarring on or around the surface of an electrode implanted into the brain for brain computer interface or brain machine interface; or for electrotherapy.

The invention will now be illustrated by the following non-limiting Examples.

EXAMPLES

Experimental (i) Preparation of Protein Coated Electrodes

Figure 3:
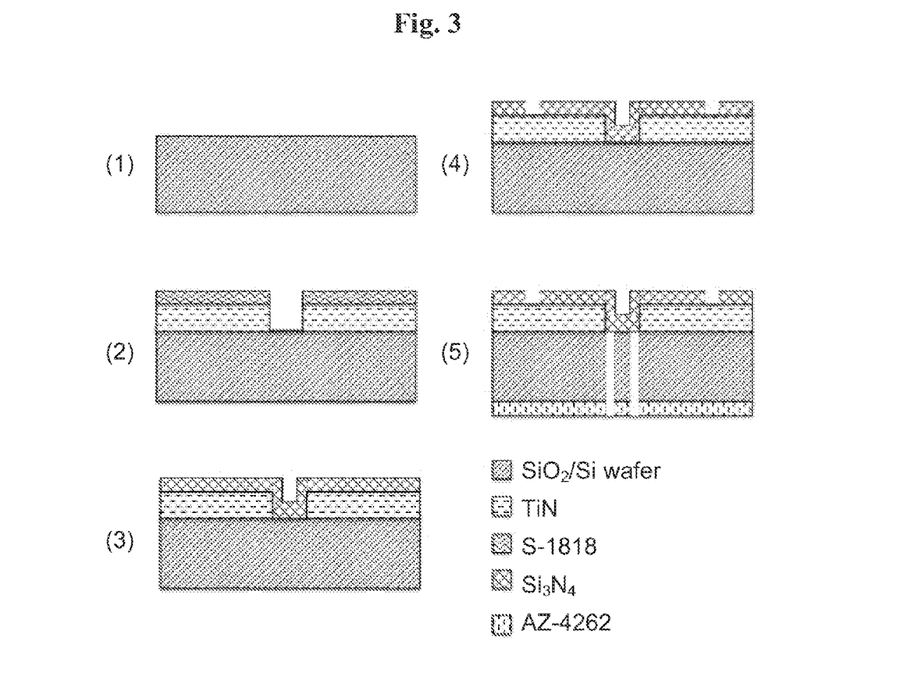
FIG. 3 shows cross-section view of the micro fabrication process: (1) cleaning of the Si wafer; (2) patterning of the metal layer and photoresist; (3) deposition of the silicon nitride insulation layer; (4 and 5) photolithography and opening of the microelectrode and contact pad areas; and (4) backside photolithography. S-1818: Shipley S1818™ positive photoresist; AZ-4262 (OPD 4262): positive photoresist developer (Fujifilm Electronic Materials U.S.A., Inc.).

Long shaft silicon (Si) electrode-array with total dimensions of 300 μm×300 μm×10000 μm was designed with 10 exposed metal pads, 20 μm×20 μm each, arranged on the penetrating tip (FIG. 1). Sputtered titanium-nitride (TiN; 300 Å) was used as the conductive material and the insulator (passivation layer) was silicon nitride ($Si_3N_4$; 150 Å). The insulation was performed by sputtering from $Si_3N_4$ target using $Ar+N_2$ plasma. FIG. 3 shows a cross-section view of the micro fabrication process.

Figure 4:
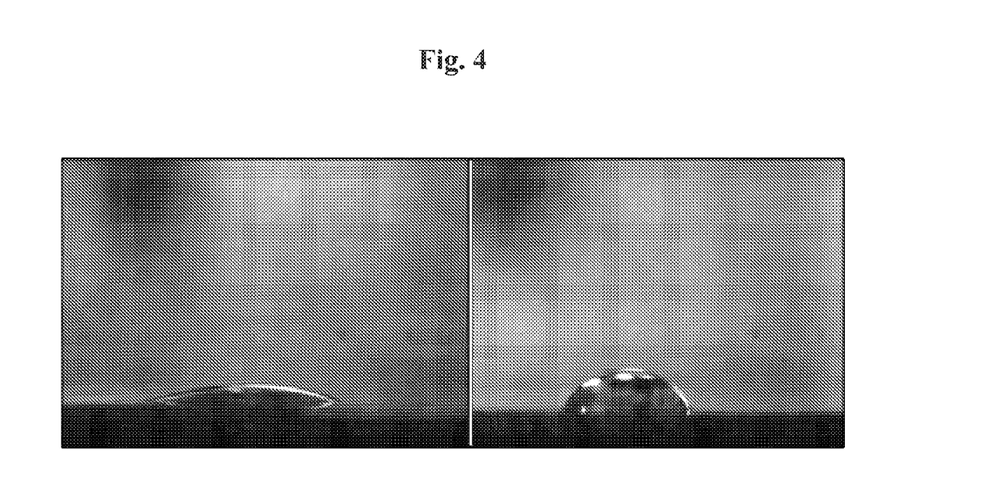
FIG. 4 shows contact angle examination of the multi-electrode array (MEA) before silanization (left panel; 17.3°) and following silanization (right panel; 61.2°).

Si electrodes were cleaned and coated according to the Radio Corporation of America (RCA) procedure detailed in Einati et al. (2009). The coating included a thin silane layer followed by the glutaraldehyde binding molecules to the protein molecules. First, electrodes were dipped in $NH_4OH$:$H_2O_2$:$H_2O$ (1:1:5, v/v/v) at 80° C. for 10 min, and were then washed three times with double distilled water (DDW); immersed in $HCl$:$H_2O_2$:$H_2O$ (1:1:6, v/v/v) at 80° C. for 10 min; and after cleaning were washed once again with DDW three times. In order to prepare the surface for the silanization, the electrodes were immersed in ethanol three times followed by 30 seconds of oxygen plasma. Self-assembled monolayer (SAM) layers were deposited using a silane compound followed by glutaraldehyde over-coating to ensure adhesion of the protein. The silane used was 3-aminopropyl-TMOS($NH_3$—$(CH_2)_3$—$Si(OCH_3)_3$), APTMS, Sigma-Aldrich) and glutaraldehyde ($OHC(CH_2)_3CHO$) was in solution with pentane-1,5-dial solution (Sigma-Aldrich). Self-assembly process was performed in closed vials containing 1% of silane in ethanol for 3 hours at 70° C. In order to obtain a well-ordered monolayer, the unbounded molecules of the organic monolayer were removed by ultrasonic agitation in ethanol, followed by baking in 100° C. for 30 minutes. The electrodes were then dipped in 10% glutaraldehyde solution for 1 hour in 37° C. and washed with PBS and DDW (18 MΩ). Contact angle measurement indicated the presence of silane molecules on the MEA with increased hydrophobic characteristics of the MEA (Brzoska et al., 1994), as shown in FIG. 4.

Figure 5:
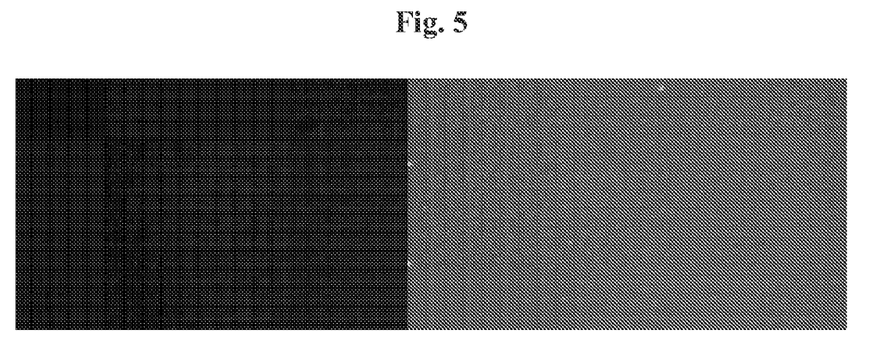
FIG. 5 shows florescent microscopy examination (×10) of the MEA without IgG (left panel) and with IgG (right panel).

The electrodes were dipped in (i) a solution of 25 μg/ml of fluorescent IgG (Biotest, Israel) in saline; (ii) a solution of 25 μg/ml of IL-1ra (Biotest, Israel) in saline; or (iii) a solution of 25 μg/ml of laminin (Biotest, Israel) in saline, for 1 hour in 37° C., and were kept in 4° C. until further use. The fluorescent IgG was used as a model demonstrating the efficacy of the coating process only. Florescent microscopy examination of the MEA following the attachment of florescent IgG confirmed marked increased fluorescent marking in the IgG coated MEA compared to non-coated areas of the same MEA, as shown in FIG. 5.

(ii) Surgical Procedures

Sprague-Dawley rats (Harlan, Israel) were tested at twelve to sixteen weeks of age. Rats were housed under reversed 12/12 hrs light/dark cycle and were given ad-libitum access to food and water. All procedures were approved by the Tel Aviv University Animal Care and Use Committee (P-17-007).

Surgical procedures were conducted as previously described (Taub and Mintz, 2010). In brief, rats were anesthetized with IP injection of ketamine hydrochloride (50 mg/kg) and xylazine (10 mg/kg). A supplement of ketamine hydrochloride (25 mg/kg) and xylazine (5 mg/kg) was applied every 30 and 60 min, respectively, and based on pain reflexes. Rat's head was shaved and skin was scrubbed using ethanol and povidone-iodine 10% (Dr. Fisher, Israel). Rat's head was positioned in a stereotaxic apparatus (Kopf Ins.; Paxinos and Watson, 2007), and the scalp was cut and retracted. A burr-hole was made bilaterally at 0.2 mm anterior and 3.0 mm lateral to the bregma, and dura was sectioned.

Electrodes were implanted using standard stereotaxic methods to 8.5 mm ventral to bregma, aiming at the dorsal endopiriform nucleus. Electrodes were fixed to the skull using dental acrylic and stainless steel screws (Plastics One, Inc., VA, USA). The skin was sutured anterior and posterior to the acrylic construction, and animals received pen-strep antibiotics (Norbrook, Ireland).

(iii) Immunohistochemistry and Data Quantification

Animals were prepared for immunohistology one or four weeks after electrode implantation. Rats were deeply anaesthetized using an overdose of sodium-pentobarbital and perfused with saline and 2.5% fresh paraformaldehyde (PFA), and brains were extracted and post-fixed in 1% fresh PFA. Glial fibrillary acidic protein (GFAP) staining is a common method for the assessment of glial scarring. To examine GFAP response, three successive 30-μm thick horizontal sections were cut through the cortex and were stained. The sections were exposed to a blocking solution made of 20% horse serum/0.1% Triton X-100 for 2 hours.

For the glial staining, polyclonal rabbit anti-GFAP was used as a primary antibody. Sections were then mounted and images were acquired (×10 and ×20; Olympus IX-70 FLA microscope with a DVC-1310C digital camera; DVC, Austin, Tex.). In order to minimize unequal illumination, all images were acquired under the same exposure and within the same day. For the image analysis, three equal size consecutive microscope images (×20) were acquired radial to the electrode insertion site for each horizontal section, and quantitative immunohistological analysis was performed using Image-ProPlus software (Media Cybernetics, Silver Spring, Md.) to measure Integrated Optical Density (IOD) of color-specific pixels. All statistical inferences were made between the IL-1ra-coated electrodes and control or laminin-coated electrodes using two-tailed paired t-test using STATISTICA software (StatSoft, Inc., Tulsa, Okla.).

Example 1

IL-1ra Coating Actively Inhibits Glial Scarring Around Implanted Electrodes

Rats (n=10) treated as described in Experimental were implanted with both IL1-ra-coated and non-coated electrodes, one in each hemisphere, and were randomly assigned to two groups, i.e., examination one or four weeks after implantation. Another group of rats (n=3) was implanted with both IL1-ra- and laminin-coated electrodes, one in each hemisphere, and were examined four weeks after implantation.

Figure 6:
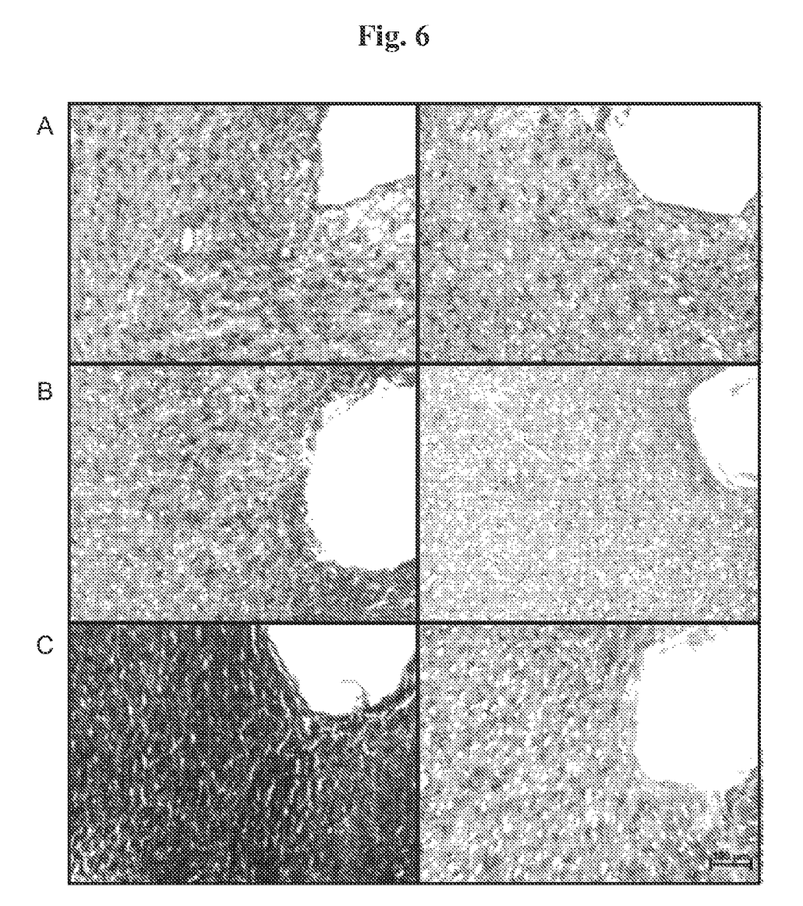
FIG. 6 shows representative microscopy (×10) of horizontal brain sections immunostained for GFAP surrounding electrode insertion sites. Panel A shows insertion sites of IL-1ra-coated (right) and non-coated (left) electrodes presented one week after implantation. Panel B shows insertion sites of IL-1ra-coated (right) and laminin-coated (left) electrodes presented four weeks after implantation. Panel C shows insertion sites of IL-1ra-coated (right) and non-coated (left) electrodes presented four weeks after implantation. Extensive scarring can be observed ~500 μm away from the insertion site as a dark belt in the vicinity of the track of the non-coated and laminin-coated electrodes, while only minor scarring can be observed for the IL-1ra-coated electrode.
Figure 7:
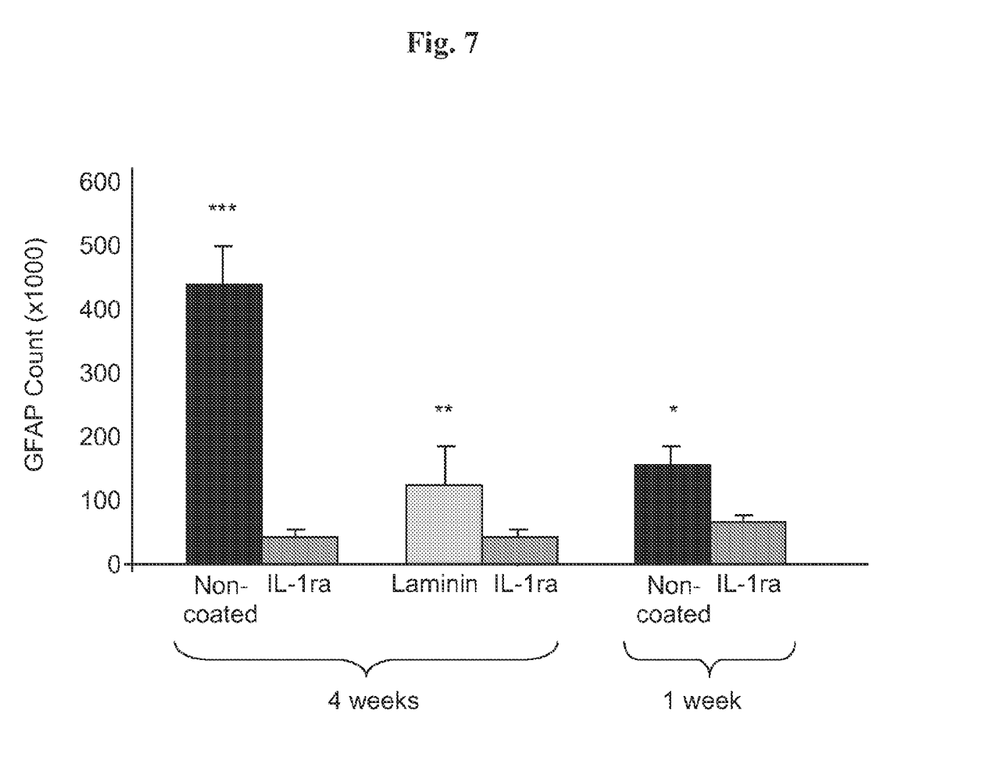
FIG. 7 shows GFAP intensity measured as integrated optic density (IOD) for the IL-1ra-coated (dark gray), laminin-coated (light gray), and non-coated (black) electrodes, presented one and four weeks post implantation. GFAP level measured at four weeks after implantation was lower in the IL-1ra-coated electrodes than that in the non-coated electrodes and laminin-coated electrodes. GFAP level measured at one week after implantation was lower in the IL-1ra-coated electrodes than that in the non-coated electrodes. *$p<0.05$, $p<0.01$, *$p<0.001$.

At one week post implantation, the GFAP stained area, measured as IOD at up to 100 μm in radius around the IL-1a-coated electrode insertion site was significantly lower than that around the non-coated electrode (n=4; p<0.05; FIG. 6, panel A) and did not differ significantly from intact cortex tissue of the same size, far away (taken from >1 mm from insertion site) (p=0.72). At four weeks post implantation, the GFAP stained area around the IL-1ra-coated electrode insertion site was significantly lower than that around the laminin-coated electrode (n=3; p<0.01; FIG. 6, panel B) and non-coated electrode (n=6; p<0.001; FIG. 6, panel C), and, in fact, did not differ significantly from intact cortex tissue far from the electrode insertion site (p=0.86; FIG. 7).

These findings indicate that by coating Si electrodes with the IL-1 antagonist IL-1ra, i.e., an inert active protein, a local suppression of glial scarring has been observed with no systemic side effects.

REFERENCES

Abbott, A., Neuroprosthetics: In search of the sixth sense. Nature, 2006, 442(7099), 125-127
Aziz, J., Abdelhalim, K., Shulyzki, R., Genov, R., Bardakjian, B., Derchansky, M., Serletis, D., Carlen, P., 256-Channel neural recording and delta compression microsystem with 3D electrodes, IEEE Journal of Solid-State Circuits, 2009, 44(3), 995-1005
Babcock, A. A., Kuziel, W. A., Rivest, S., Owens, T., Chemokine expression by glial cells directs leukocytes to sites of axonal injury in the CNS. The Journal of Neuroscience, 2003, 23(21), 7922-7930
Bendele, A. M., Chlipala, E. S., Scherrer, J., Frazier, J., Sennello, G., Rich, W. J., Edwards III, C. K., Combination benefit of treatment with the cytokine inhibitors interleukin-1 receptor antagonist and PEGylated soluble tumor necrosis factor receptor type I in animal models of rheumatoid arthritis. Arthritis & Rheumatism, 2000, 43(12), 2648-2659
Born, T. L., Smith, D. E., Garka, K. E., Renshaw, B. R., Bertles, J. S., Sims, J. E., Identification and characterization of two members of a novel class of the interleukin-1 receptor (IL-1R) family. Journal of Biological Chemistry, 2000, 275(39), 29946-29954
Brzoska, J. B., Azouz, I. B., Rondelez, F., Silanization of solid substrates: a step toward reproducibility. Langmuir, 1994, 10(11), 4367-4373
Chabot, S., Williams, G., Yong, V. W., Microglial production of TNF-alpha is induced by activated T lymphocytes. Involvement of VLA-4 and inhibition by interferonbeta-1b. Journal of Clinical Investigation, 1997, 100(3), 604-612
Chua, P. H., Neoh, K. G., Kang, E. T., Wang, W., Surface functionalization of titanium with hyaluronic acid/chitosan polyelectrolyte multilayers and RGD for promoting osteoblast functions and inhibiting bacterial adhesion. Biomaterials, 2008, 29, 1412-1421
Einati, H., Mottel, A., Inberg, A., Shacham-Diamand, Y., Electrochemical studies of self-assembled monolayers using impedance spectroscopy. Electrochim. Acta, 2009, 54, 6063-6069
Eng, L. F., Ghirnikar, R. S., GFAP and astrogliosis. Brain Pathology, 1994, 4(3), 229-237
Eng, L. F., Ghirnikar, R. S., Lee, Y. L., Glial fibrillary acidic protein: GFAP-thirty-one years (1969-2000). Neurochem. Res., 2000, 25(9-10), 1439-1451
Giulian, D., Tapscott, M. J., Immunoregulation of cells within the central nervous system. Brain, Behavior, and Immunity, 1988, 2(4), 352-358
Giulian, D., Li, J., Leara, B., Keenen, C., Phagocytic microglia release cytokines and cytotoxins that regulate the survival of astrocytes and neurons in culture. Neurochemistry International, 1994a, 25(3), 227-233
Giulian, D., Li, J., Li, X., George, J., Rutecki, P. A., The impact of microglia-derived cytokines upon gliosis in the CNS. Developmental Neuroscience, 1994b, 16(3-4), 128-136
Griffith, R. W., Humphrey, D. R., Long-term gliosis around chronically implanted platinum electrodes in the Rhesus macaque motor cortex. Neuroscience Letters, 2006, 406 (1-2), 81-86
He, W., McConnell, G. C., Bellamkonda, R. V., Nanoscale laminin coating modulates cortical scarring response around implanted silicon microelectrode arrays. Journal of Neural Engineering, 2006, 3(4), 316-326
House, P. A., MacDonald, J. D., Tresco, P. A., Normann, R. A., Acute microelectrode array implantation into human neocortex: preliminary technique and histological considerations. Neurosurg Focus, 2006, 20(5), E4
Hughes, P. S., Krcek, J. P., Hobson, D. E., Del Bigio, M. R., An unusual inflammatory response to implanted deep brain electrodes. The Canadian Journal of Neurological Sciences. Le Journal Canadien Des Sciences Neurologiques, 2011, 38(1), 168-170
Kim, D. H., Martin, D. C., Sustained release of dexamethasone from hydrophilic matrices using PLGA nanoparticles for neural drug delivery. Biomaterials, 2006, 27(15), 3031-3037
McConnell, G. C., Rees, H. D., Levey, A. I., Gutekunst, C. A., Gross, R. E., Bellamkonda, R. V., Implanted neural electrodes cause chronic, local inflammation that is correlated with local neurodegeneration. Journal of Neural Engineering, 2009, 6(5), 056003
Morgan, M. P., Whelan, L. C., Sallis, J. D., McCarthy, C. J., Fitzgerald, D. J., McCarthy, G. M., Basic calcium phosphate crystal-induced prostaglandin E2 production in human fibroblasts: role of cyclooxygenase 1, cyclooxygenase 2, and interleukin-1β. *Arthritis Rheum.*, 2004, 50(5), 1642-1649

Nicolelis, M. A. L., Chronic, multisite, multielectrode recordings in macaque monkeys. *Proceedings of the National Academy of Sciences*, 2003, 100(19), 11041-11046

Nordhausen, C., Maynard, E., Normann, R., Single unit recording capabilities of a 100 microelectrode array. *Brain Research*, 1996, 726(1-2), 129-140

Otani, Y., Tabata, Y., Ikada, Y., A new biological glue from gelatin and poly (L-glutamic acid). *Journal of Biomedical Materials Research*, 1996, 31, 158-166

Paxinos, G., Watson, C., *The rat brain in stereotaxic coordinates.* 6$^{th}$ ed. San Diego, Calif.: Academic Press; 2007

Polikov, V., Tresco, P., Reichert, W., Response of brain tissue to chronically implanted neural electrodes. *Journal of Neuroscience Methods*, 2005, 148(1), 1-18

Polikov, V. S., Block, M. L., Fellous, J. M., Hong, J. S., Reichert, W. M., In vitro model of glial scarring around neuroelectrodes chronically implanted in the CNS. *Biomaterials*, 2006, 27(31), 5368-5376

Santhanam, G., Yu, B. M., Gilja, V., Ryu, S. I., Afshar, A., Sahani, M., Shenoy, K. V., A factor-analysis decoder for high-performance neural prostheses. *Proc. of the IEEE International Conference on Acoustics, Speech, and Signal Processing (ICASSP)*, Las Vegas, Nev., 2008, 5208-5211

Sheng, W., Hu, S., Kravitz, F., Peterson, P., Chao, C., Tumor necrosis factor alpha upregulates human microglial cell production of interleukin-10 in vitro. *Clin. Diagn. Lab. Immunol.*, 1995, 2(5), 604-608

Spataro, L., Dilgen, J., Retterer, S., Spence, A. J., Isaacson, M., Turner, J. N., Shain, W., Dexamethasone treatment reduces astroglia responses to inserted neuroprosthetic devices in rat neocortex. *Experimental Neurology*, 2005, 194(2), 289-300

Tate, M., Biocompatibility of methylcellulose-based constructs designed for intracerebral gelation following experimental traumatic brain injury. *Biomaterials*, 2001, 22(10), 1113-1123

Taub, A. H., Mintz, M., Amygdala conditioning modulates sensory input to the cerebellum. *Neurobiology of Learning and Memory*, 2010, 94(4), 521-529

Thompson, R. C., Dripps, D. J., Eisenberg, S. P., Interleukin-1 receptor antagonist (IL-1ra) as a probe and as a treatment for IL-1 mediated disease. *International Journal of Immunopharmacology*, 1992, 14(3), 475-480

Turner, D. A., Patil, P. G., Nicolelis, M. A. L., *Conceptual and Technical Approaches to Human Neural Ensemble Recordings.* Frontiers in neuroscience (2nd ed.), 2008, Boca Raton, Fla.: CRC Press.

Wider, C., Pollo, C., Bloch, J., Burkhard, P. R., Vingerhoets, F. J. G., Long-term outcome of 50 consecutive Parkinson's disease patients treated with subthalamic deep brain stimulation. *Parkinsonism & Related Disorders*, 2008, 14(2), 114-119

Wolpaw, J. R., McFarland, D. J., Control of a two-dimensional movement signal by a noninvasive brain-computer interface in humans. *Proceedings of the National Academy of Sciences of the United States of America*, 2004, 101(51), 17849-17854

Woodroofe, M. N., Sarna, G. S., Wadhwa, M., Hayes, G. M., Loughlin, A. J., Tinker, A., Cuzner, M. L., Detection of interleukin-1 and interleukin-6 in adult rat brain, following mechanical injury, by in vivo microdialysis: evidence of a role for microglia in cytokine production. *Journal of Neuroimmunology*, 1991, 33(3), 227

The invention claimed is:

1. An electrode designed for implantation into the central nervous system (CNS) of a mammal, said electrode comprising:
(i) a sole electrical lead coated with an insulator forming a passivation layer, or multiple electrical leads each being either coated with an insulator forming a passivation layer or imprinted on a carrier and coated with an insulator forming a passivation layer;
(ii) an adhesive layer consisting of an upper adhesive layer and optionally a lower adhesive layer; and
(iii) interleukin-1 receptor antagonist (IL-1ra), wherein said lower adhesive layer, when present, is covalently linked to the surface of said passivation layer; said upper adhesive layer is covalently linked to said lower adhesive layer, when present, or to the surface of said passivation layer; and the IL-1ra is covalently linked to said upper adhesive layer and actively inhibits scarring on or around the surface of said electrode when implanted into the CNS.

2. The electrode according to claim 1, comprising the multiple electrode leads imprinted on the carrier, wherein said carrier is coated with said insulator.

3. The electrode according to claim 1, wherein:
(i) said insulator is a silicon-based insulator, metal oxide, or polymer;
(ii) said lower adhesive layer, when present, comprises amino functional alkoxysilane, mercapto functional alkoxysilane, aminoalkanethiol, carboxyalkanethiol, carboxyalkyldisulfide, succinimidyl ester, or ferrocenylalkanethiol;
(iii) said upper adhesive layer comprises succinaldehyde, glutaraldehyde, adipaldehyde, heptanedial, octanedial, cyanoacrylate type adhesives, fibrin glue, gelatin-resorcin aldehyde type adhesives, or polyelectrolyte multilayers of hyaluronic acid and chitosan, coupled with surface-immobilized cell-adhesive arginine-glycine-aspartic acid peptide;
(iv) said carrier is a silicon-based insulator, metal oxide, or polymer; or
(v) each one of said electrical leads is made of a material selected from the group consisting of a metal, preferably a noble metal, a metal alloy, a metalloid, and a conducting ceramic material.

4. The electrode according to claim 3, wherein:
(i) said silicon-based insulator is silicon nitride, silicon dioxide, or silicon oxynitride; said metal oxide is aluminum oxide, tantalum oxide, or hafnium oxide; and said polymer is a polyimide, or a plastic;
(ii) said metal is gold, platinum, iridium, osmium, silver, palladium, rhodium or ruthenium, mercury, polonium, copper, bismuth, technetium, rhenium, or antimony;
(iii) said metal alloy is selected from the group consisting of nitrides of refractory metals, metal borides, metal carbides, metal silicides, beryllides, metal selenides, metal phosphides, metal chromides, mixtures of the aforesaid, ternary alloys of the aforesaid with other elements, non-toxic nickel alloys, and quaternary alloys;
(iv) said metalloid is boron, silicon, germanium, arsenic, antimony, tellurium, or polonium; or
(v) said conducting ceramic material is a metal nitride, a metal carbide, a metal boride, a metal silicide, a metal beryllide, a metal selenide, a metal phosphide, a metal chromate, a metal-silicon nitride, a metal-silicon carbide, a metal-silicon boride, or a mixture thereof.

5. The electrode according to claim 3, wherein: (i) said amino functional alkoxysilane has the formula $H_2N$—$(C_1$-$C_8)$alkylene-$Si(OR_1)_3$ or $H_2N$—$(C_1$-$C_8)$alkylene-$SiR_2(OR_1)_2$; (ii) said mercapto functional alkoxysilane has the formula HS—$(C_1$-$C_8)$alkylene-$Si(OR_1)_3$ or HS—$(C_1$-$C_8)$alkylene-$SiR_2(OR_1)_2$; (iii) said aminoalkanethiol has the formula $H_2N$—$(C_1$-$C_8)$alkylene-SH; (iv) said carboxyalkanethiol has the formula HOOC—$(C_1$-$C_8)$alkylene-SH; (v) said hydroxyalkanethiol has the formula HO—$(C_1$-$C_8)$alkylene-SH; (vi) said carboxyalkyldisulfide has the formula HOOC—$(C_1$-$C_8)$alkylene-S—S—$(C_1$-$C_8)$alkylene-COOH; or (vii) said ferrocenylalkanethiols has the formula ferrocenyl-$(C_1$-$C_8)$alkylene-SH, wherein $R_1$ each independently is $(C_1$-$C_4)$alkyl; and $R_2$ each independently is $(C_1$-$C_4)$alkyl or H.

6. The electrode according to claim 3, wherein said insulator is silicon nitride; said lower adhesive layer comprises 3-aminopropyltrimethoxysilane; said upper adhesive layer comprises glutaraldehyde; or said electrical lead each is made of titanium-nitride.

7. The electrode according to claim 3, wherein said metal is a noble metal.

8. The electrode according to claim 1, comprising a multi-channel with the multiple electrical leads, optionally configured as an implantable multi electrode array (MEA) and are imprinted on a carrier and coated with said insulator forming a passivation layer.

9. The multi-channel electrode according to claim 8, comprising 4, 5, 6, 7, 8, 9, 10, 11, 12, 13, 14, 15, 16, 17, 18, 19, or 20 electrical leads, optionally configured as an implantable MEA, having a long shaft.

10. The multi-channel electrode according to claim 5, configured as an implantable MEA and comprising:
    (i) 10 electrical leads arranged on a penetrating tip, wherein said electrical leads are made of a conductive ceramic material, imprinted on silicon nitride as a carrier and coated with silicon nitride as an insulator forming a passivation layer; or
    (ii) 14 electrical leads arranged on a penetrating tip, wherein said electrical leads are made of a noble metal, imprinted on and coated with a polyimide.

11. The multi-channel electrode according to claim 10, wherein said conductive ceramic material is titanium-nitride.

12. The electrode according to claim 1, wherein said electrode is a single-shank electrode, or a member of a vector electrode or a three-dimensional electrode.

13. The electrode according to claim 1, wherein each one of said electrical leads is made of titanium-nitride; said insulator is silicon nitride; said lower adhesive layer comprises 3-aminopropyltrimethoxysilane; said upper adhesive layer comprises glutaraldehyde; and said carrier, when present, is made of silicon nitride.

14. The electrode according to claim 1, comprising a single channel with the sole electrical lead.

15. A method for central nervous system (CNS) recording and/or CNS stimulation in an individual suffering from a CNS dysfunction, disease or disorder, or CNS injury, said method comprising the steps of:
    implanting into the CNS of said individual at least one electrode each independently according to claim 1; and
    recording and/or stimulating said CNS with said at least one electrode.

16. The method of claim 15, wherein the at least one electrode is implanted in deep brain structures, further comprising receiving signals from the at least one electrode for deep brain recording, transmitting signals to the at least one electrode for deep brain stimulation, or both receiving signals from and transmitting signals to the at least one electrode for both deep brain recording and deep brain stimulation.

17. The method of claim 16, wherein the signals are received and/or transmitted in a manner configured for (i) treatment of a brain dysfunction, a brain disease or disorder, or a brain injury; (ii) electrotherapy; or (iii) establishing a brain computer interface, or a brain machine interface.

18. The method of claim 17, wherein (a) the individual is in need of treatment of said brain dysfunction, wherein said brain dysfunction is associated with an autoimmune disease, head trauma or neuronal trauma, or said brain dysfunction causes chronic pain or phantom limb pain; or (b) the individual is in need of treatment of said brain disease or disorder, wherein said brain disease or disorder is Parkinson's disease, epilepsy, dystonia, essential tremor, Tourette syndrome, a mental disorder, or an anxiety disorder; or said brain disease or disorder is associated with brain degradation or age-related brain degeneration.

19. The method of claim 15, wherein in said at least one electrode said insulator is silicon nitride; said lower adhesive layer comprises 3-aminopropyltrimethoxysilane; said upper adhesive layer comprises glutaraldehyde; or said electrical lead each is made of titanium-nitride.

20. The method of claim 15, wherein in said at least one electrode each one of said electrical leads is made of titanium-nitride; said insulator is silicon nitride; said lower adhesive layer comprises 3-aminopropyltrimethoxysilane; said upper adhesive layer comprises glutaraldehyde; and said carrier, when present, is made of silicon nitride.

21. The method of claim 15, wherein said at least one electrode is a single-channel electrode comprising a sole electrical lead.

22. The method of claim 15, wherein said at least one electrode is a multi-channel electrode comprising multiple electrical leads, optionally configured as an implantable multi electrode array (MEA) wherein said electrical leads are imprinted on a carrier and coated with said insulator forming a passivation layer.

* * * * *

UNITED STATES PATENT AND TRADEMARK OFFICE
CERTIFICATE OF CORRECTION

PATENT NO. : 9,517,020 B2
APPLICATION NO. : 14/236853
DATED : December 13, 2016
INVENTOR(S) : Yosi Shacham-Diamand Page 1 of 1

It is certified that error appears in the above-identified patent and that said Letters Patent is hereby corrected as shown below:

On the Title Page

In Column 1 (page 2, item (56)) at Line 28, Under Other Publications, Change "Chord" to --Cord--.

In Column 2 (page 2, item (56)) at Line 43, Under Other Publications, Change "spectroscophy," to --spectroscopy,--.

In the Specification

In Column 1 at Line 50, Change "computerr" to --computer--.

In Column 5 at Line 48, Change "IL-1a" to --IL-1α--.

In Column 8 at Line 12, Change "pyrrolidonene," to --pyrrolidinone,--.

In Column 8 at Line 12, Change "polyamid" to --polyamide--.

In Column 10 at Line 21, Change "undecanate);" to --undecanoate);--.

In the Claims

In Column 20 at Line 25, In Claim 2, change "electrode" to --electrical--.

In Column 20 at Lines 45-46, In Claim 3, after "metal," delete "preferably a noble metal,".

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*